United States Patent [19]

Diefenbach

[11] 4,364,873

[45] Dec. 21, 1982

[54] METHOD OF MAKING ALUMINUM ALKYLS

[75] Inventor: Steven P. Diefenbach, Baton Rouge, La.

[73] Assignee: Ethyl Corporation, Richmond, Va.

[21] Appl. No.: 282,494

[22] Filed: Jul. 13, 1981

[51] Int. Cl.$^3$ ................................................. C07F 5/06
[52] U.S. Cl. ................................................. 260/448 A
[58] Field of Search .................................... 260/448 A

[56] References Cited

U.S. PATENT DOCUMENTS

| | | | |
|---|---|---|---|
| 2,691,668 | 10/1954 | Ziegler et al. | 260/448 A |
| 2,744,127 | 5/1956 | Ziegler et al. | 260/448 A |
| 2,839,556 | 6/1958 | Ziegler et al. | 260/448 A |
| 2,863,894 | 12/1958 | Smith | 260/448 A |
| 2,931,820 | 4/1960 | Barclay et al. | 260/448 A |
| 4,118,409 | 10/1978 | Eidt et al. | 260/448 A |

*Primary Examiner*—Helen M. S. Sneed
*Attorney, Agent, or Firm*—Donald L. Johnson; John F. Sieberth; Paul H. Leonard

[57] ABSTRACT

A method of making trimethylaluminum wherein a trialkylaluminum having at least two carbon atoms in the alkyl group is reacted with a methyl halide in the presence of a vanadium-based catalyst to form trimethylaluminum and an alkyl halide.

27 Claims, No Drawings

METHOD OF MAKING ALUMINUM ALKYLS

BACKGROUND OF THE INVENTION

Field of the Invention

The present invention relates to a method of making aluminum alkyls or alkyl aluminum compounds and especially to the making of trimethylaluminum.

A variety of processes are known for the preparation of aluminum alkyls and for the preparation of trimethylaluminum in particular. Decomposition reactions of aluminum alkyls with alkyl halides are documented in the literature.

One preferred method for making trimethylaluminum involves the sodium reduction of methylaluminum sesquichloride. Such procedure is an expansive one. Processes of this type are described in British Pat. No. 762,200 and U.S. Pat. No. 2,954,389 and in an article by A. V. Grosse and J. M. Mavity, *Journal of Organic Chemistry*, 5, 106 (1940). Preparation of trimethylaluminum has also been carried out by the sodium reduction of dimethylaluminum chloride as described in an article by S. Pasynkiewicz and M. Boleslawski, *Journal of Organometallic Chemistry*, 25, 29 (1970). The methods described in the foregoing articles each form a basis for existing commercial processes for the production of trimethylaluminum, but each produce non-usable by-products having limited value in vast quantities in comparison to the trimethylaluminum produced. The by-products produced by the above processes are aluminum and sodium chloride.

The several processes that have utilized the above sodium reduction reactions suffer from an inherent problem in that trimethylaluminum will itself react with sodium to produce sodium tetramethylaluminate, a compound that, unless it reacts with dimethylaluminum chloride will cause reduced yields and present a disposal problem. Sodium tetramethylaluminate is extremely reactive towards moisture in the air, as would excess unreacted sodium. The disposal problems presented by these two compounds represent a significant proportion of the cost of production of trimethylaluminum manufactured by such processes.

Although the conversion of dimethylaluminum chloride to trimethylaluminum without the use of sodium (Cryolite Process) is described in U.S. Pat. No. 2,839,556, this reaction scheme produces a vast amount of solid by-product having limited commercial value.

Two other methods for production of aluminum trialkyls are described in an article by R. Koster and P. Binger, *Advances in Inorganic and Radiochemistry*, I, 1263 (1965) and by K. S. Pitzer and H. S. Gutowsky, *Journal of American Chemical Society*, 68, 2204 (1946). Both of these methods suffer from the use of expensive starting materials and the production of non-useful or extremely reactive by-products requiring expensive process equipment and handling techniques.

U.S. Pat. No. 2,744,127 describes a relatively simple process for the preparation of trimethylaluminum which produces as a by-product magnesium chloride in the weight ratio 2.7:1 magnesium chloride:trimethylaluminum. The magnesium chloride has little or no commercial value.

A process for producing a mono-hydrocarbon aluminum dihalide is disclosed in U.S. Pat. No. 2,270,292. In such process, a hydrocarbon halide is reacted with metallic aluminum to form a dihydrocarbon-aluminum-mono-halide and the latter is then reacted with an aluminum trihalide to form the desired dihalide product.

U.S. Pat. No. 2,863,894 relates to a process for producing aluminum alkyls, wherein aluminum is reacted with a primary alkyl halide, including methyl iodide in the presence of an inert, aromatic-free solvent to form a solution of sesquihalide dissolved in the inert solvent and then reacting the sesquihalide with an alkali metal to form the aluminum alkyl.

A more recent patent, U.S. Pat. No. 4,118,409, provides for jointly making trimethylaluminum and alkylaluminum bromides and iodides by mixing an aluminum trialkyl and a methylaluminum bromide or iodide and then distilling from the mixture trimethylaluminum as a first fraction and then alkylaluminum bromides or iodides as a subsequent fraction. The alkylaluminum halides used in such a redistribution process are themselves expensive compounds.

SUMMARY OF THE INVENTION

The present invention relates to a process for making trimethylaluminum, wherein a trialkyl aluminum having at least two carbon atoms in the alkyl group is reacted with a methyl halide in the presence of a vanadium-based catalyst to form a trimethylaluminum and an alkyl halide.

DESCRIPTION OF THE PREFERRED EMBODIMENTS

It has been discovered that trimethylaluminum can be prepared by a catalyzed exchange reaction between methyl bromide or methyl chloride and triethylaluminum. The catalyst employed is a vanadium-based one and is defined hereinafter. Yields of about 85 percent trimethylaluminum and ethyl bromide were obtained using methyl bromide as a reactant and a vanadium-based catalyst comprised of ethyl iodide, vanadium oxytrichloride and triethylaluminum. Although not wishing to be bound by any particular theory, it is believed that the first step of the catalytic cycle converts a portion of the methyl halide, i.e., methyl bromide or methyl chloride to methyl iodide.

The vanadium-based or vanadium component catalyst is prepared by charging a pressure vessel with an alkyl iodide, adding the vanadium compound, and then an alkyl aluminum compound. The alkyl iodide should be present in a sufficient amount to provide a slurry. Generally, the alkyl aluminum compound used is on a one to one mole basis with the vanadium compound. Sufficient amounts of each component comprising the catalyst must be present in amounts necessary to provide an active catalyst.

Ethyl iodide is the preferred alkyl iodide for the catalyst composition. Other suitable iodides are methyl iodide and alkyl iodides having up to about 18 carbon atoms in the alkyl group.

Preferred aluminum alkyls as a catalyst component are trimethylaluminum and triethylaluminum. Other suitable alkyl aluminum compounds are the commercially available trialkylaluminum compounds such as tri-isobutylaluminum, tri-n-butylaluminum, tri-n-hexylaluminum and tri-n-octylaluminum. Additional suitable alkyl aluminum compounds are alkyl aluminum halides such as diethylaluminum iodide and diethylaluminum chloride.

In addition to vanadium oxytrichloride ($VOCl_3$) which is the most preferred vanadium compound used in preparing the vanadium-based catalyst, other suitable vanadium compounds are vanadium trichloride (VCl₃), vanadium oxytribromide (VOBr₃) and vanadium tribromide (VBr₃). Suitable organic vanadium compounds are vanadium alkylates [V(OR)₄, e.g., vanadium ethylate (C₂H₅O)₄V] and vanadium oxyalkylates [VO(OR)₃, e.g., vanadium oxytriethylate (C₂H₅O)₃OV].

Optionally, alkyl iodide can be removed and the catalyst can be reactivated by addition of trialkylaluminum or a mixture of trialkylaluminum and alkyl iodide.

In the preferred form of the invention, trimethylaluminum is prepared by a thermal alkyl group catalyzed exchange reaction between triethylaluminum and methyl halide utilizing a vanadium-based catalyst. The following equation represents the reaction:

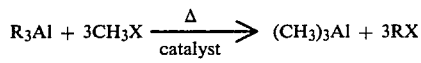

$$R_3Al + 3CH_3X \xrightarrow[\text{catalyst}]{\Delta} (CH_3)_3Al + 3RX$$

wherein
R = C₂H₅ to C₄H₉
X = bromine, chlorine
Catalyst = vanadium compound based.

When the alkyl group is ethyl, the exchange proceeds at 65°–75° C. The exchange is quite selective and gives high conversion to trimethylaluminum when methyl bromide is used.

The foregoing reaction offers an economically attractive synthetic route to the preparation of trimethylaluminum and/or long-chain alkyl halides.

The invention will be further understood from the following examples:

GENERAL

Reactants used were commercially available products and were used as received unless otherwise noted. Methyl chloride and all aluminum alkyl compounds were products of Ethyl Corporation. Methyl iodide, ethyl iodide and ethyl bromide were purchased from Aldrich. Methyl bromide was obtained from Matheson. Cyclohexane was deoxygenated and stored over molecular sieves. Tetrahydrofuran (THF) was dried over calcium hydride and distilled under nitrogen before use. NMR (Nuclear Magnetic Resonance) spectra were recorded on a Varian EM-390 90 MHz spectrometer.

General Procedure for the Triethylaluminum-Methyl Halide (Chloride or Bromide) Catalytic Exchange The general procedure for the catalytic exchange (Table I) consisted of charging a Fisher-Porter pressure vessel with 25 mmoles (57 mol %) of alkyl iodide followed by the addition of 1.0 mmole (4.6 mol %) of the vanadium compound, then 1.0 mmole (4.6 mol %) of aluminum alkyl. Once the black slurry formed, 21.9 mmoles of triethylaluminum was added. After coolring the slurry to −78° C., ~100 mmoles of methyl halide was added. The reaction was then conducted under conditions shown in Table I. Upon completion, the slurry was usually black in methyl chloride reactions and grey in methyl bromide reactions. After cooling to room temperature, the vessel was transferred to the dry box. Excess gases were vented. An ~1 ml aliquot of the mixture was filtered through a Millipore Swinnex filter disc containing a Mitex filter into an NMR tube. The triethylaluminumtrimethylaluminum ratio was determined by NMR integration to calculate the percent exchange (Table I). Only a crude approximation could be obtained for experiments using methyl chloride because of lack of a suitable internal standard. Cyclohexane was found to be a suitable standard for experiments with methyl bromide. When the exchange reactions were tried in the presence of a few mole percent of aromatic hydrocarbons (as internal NMR standards), only decomposition to unidentifiable products occurred. Table I lists some variations in reaction conditions and catalyst component concentrations. It should be noted that when the exchange reaction is carried out at 25° C., methyl iodide is the only observed product. Several exchange reactions were tried using various compounds in lieu of the vanadium compounds as catalyst components. No exchange products were observed in such tests.

TABLE I

TRIETHYLALUMINUM-METHYL HALIDE CATALYTIC EXCHANGE
Et₃Al + MeX → ⅓Me₃Al + ⅓EtX[a]

| Run No. | MeX | Catalyst (mole percent)[b] | Conditions | Percent Exchange[c] |
|---|---|---|---|---|
| (1) | MeCl | | 90° C., 48 hrs (THF) | 0 |
| (2) | MeCl | AlCl₃ | 65° C., 6 hrs | 0 |
| (3) | MeCl | Et₂AlI(6.8) | 92° C., 16.5 hrs | 0 |
| (4) | MeCl | EtI—VCl₃—Et₃Al(57:4.6:4.6) | 75° C., 24 hrs | 15 |
| (5) | MeCl | EtI—VCl₃—Et₃Al(57:4.6:4.6) | 85° C., 6 hrs | 23 |
| (6) | MeCl | EtI—VCl₄—Et₂AlI(228:4.6:4.6) | 75° C., 20 hrs | <5 |
| (7) | MeCl | EtI—VCl₄—Et₂AlI(228:4.6:4.6) | 25° C., 66 hrs | 36 |
| (8) | MeCl | VCl₄—Et₂AlI(4.6:4.6) | 25° C., 18 hrs | 0 |
| (9) | MeCl | EtI—VCl₄—Et₂AlI(13.7:3.4:3.4) | 25° C., 18 hrs (C₆H₁₂) | <5 |
| (10) | MeCl | EtI—VCl₄—Et₂AlI(85.6:3.4:3.4) | 25° C., 24 hrs (C₆H₁₂) | 25 |
| (11) | MeCl | EtI—VCl₄—Et₂AlI(171:3.4:3.4) | 25° C., 18 hrs | 26 |
| (12) | MeCl | EtI—VOCl₃—Et₂AlI(57:4.6:4.6) | 65° C., 4 hrs | 50 |
| (13) | MeCl | EtI—VOCl₃—Et₂AlI(57:4.6:4.6) | 75° C., 21 hrs | 50 |
| (14) | MeCl | EtI—VOCl₃—Et₃Al(57:4.6:4.6) | 25° C., 66 hrs | 17 |
| (15) | MeBr | EtI—VOCl₃—Et₃Al(57:4.6:4.6) | 75° C., 16 hrs | 88 |
| (16) | MeBr | EtI—VOCl₃—Et₃Al(57:4.6:4.6) | 25° C., 16 hrs | 0[d] |
| (17) | MeBr | EtI—VOCl₃—Et₃Al(57:4.6:4.6) | 75° C., 22 hrs | 80 |
| (18) | MeBr | EtI—VCl₃—Et₃Al(57:4.6:4.6) | 75° C., 18 hrs | 45 |
| (19) | MeBr | EtI—VCl₃—Et₂AlI(57:4.6:4.6) | 75° C., 16 hrs | 33 |
| (20) | MeBr | EtI—VOCl₃—Et₃Al(4.6:4.6:4.6) | 75° C., 16 hrs | 26[e] |
| (21) | MeBr | EtI—VOCl₃—Me₃Al(4.6:4.6:9.1) | 75° C., 5 hrs | >85[f] |
| (22) | MeI | VCl₄—Et₃Al(4.6:4.6) | 25° C., 18 hrs | 30 |

TABLE I-continued
TRIETHYLALUMINUM-METHYL HALIDE CATALYTIC EXCHANGE
$Et_3Al + MeX \rightarrow 3Me_3Al + 3EtX^a$

| Run No. | MeX | Catalyst (mole percent)[b] | Conditions | Percent Exchange[c] |
|---|---|---|---|---|
| (23) | MeBr | EtI—VOCl$_3$—Et$_3$Al(4.6:4.6:4.6) | 75° C., 3 hrs | 24[f] |

[a] Et = Ethyl (C$_2$H$_5$); Me = Methyl (CH$_3$); X = Halide (Br or Cl)
[b] The mole percent is based on the initial concentration of Et$_3$Al.
[c] For reactions with MeCl, the percent exchange was approximated from the Et$_3$Al:Me$_3$Al ratio. For reactions with MeBr, the percent exchange was calculated from the NMR integration versus a cyclohexane standard.
[d] The only observable product in this reaction was MeI.
[e] The catalyst slurry was prepared as described in the experimental section, then excess EtI was evaporated under nitrogen to give a blank residue. Et$_3$Al was added directly to the residue.
[f] These reactions were run as in (e), but an EtI—Et$_3$Al solution was added to the residue (see experimental section).

EXAMPLE 1

Triethylaluminum was reacted with an excess of methyl bromide using a catalyst comprising a mixture of ethyl iodide-vanadium oxytrichloride-triethylaluminum or ethyl iodide-vanadium oxytrichloride-trimethylaluminum. The reactions were carried out at 75° C. for 16 hours and at 75° C. for five hours, respectively. Yields of ethyl bromide and trimethylaluminum were ~85 percent. Similar experiments using methyl chloride in lieu of methyl bromide produced little or no trimethylaluminum. At 90° C. without the catalyst, triethylaluminum and methyl bromide or methyl chloride failed to react. No exchange was found when carrying out the reactions using methyl chloride in tetrahydrofuran, cyclohexane, or toluene.

EXAMPLE 2

Triethylaluminum was reacted with methyl iodide at 25° C. in the presence of a vanadium tetrachloride-triethylaluminum catalyst. Yields of ~30 percent of trimethylaluminum and ethyl iodide were obtained. Similar exchange reactions without the catalyst gave ~11 percent yields of trimethylaluminum and ethyl iodide.

EXAMPLE 3

Triethylaluminum was reacted with methyl bromide at 25° C. in the presence of an ethyl iodide-vanadium oxytrichloride-triethylaluminum catalyst mixture. The only observable product was methyl iodide.

EXAMPLE 4

A vanadium-based catalyst was prepared by adding one mmole of vanadium oxytrichloride to 12.5 mmoles of ethyl iodide (deep red solution) followed by one mmole of diethylaluminum iodide giving a purple slurry. To one mmole of the purple slurry was added a reaction mixture containing 21.9 mmoles of triethylaluminum followed by 100 mmoles of methyl chloride. The mixture was held at 65° C. for four hours. Substantial formation of trimethylaluminum and methyl iodide was noted.

EXAMPLE 5

Triethylaluminum was reacted with methyl bromide at 75° C. in the presence of ethyl iodide-vanadium oxytrichloride-triethylaluminum catalyst mixture. After 1.5 hours, about 20 percent trimethylaluminum was formed. After 22 hours, the exchange was almost complete. Yields of ethyl bromide and trimethylaluminum were 80–85 percent (by NMR).

EXAMPLE 6

Example 5 was repeated with bromobenzene in lieu of methyl bromide. After five hours at 75° C. or 16 hours at 25° C., no evidence of exchange was observed.

EXAMPLE 7

Methyl chloride was reacted with triethylaluminum using the vanadium oxytrichloride catalyst system at 65°–75° C. After 20 hours, yields of 50–60 percent trimethylaluminum was observed. Under similar conditions, substituting methyl bromide for methyl chloride gave yields of 80–85 percent trimethylaluminum. Related systems using vanadium trichloride as catalyst showed much less activity. A vanadium tetrachloride-diethylaluminum iodide catalyst in a similar system was ineffective.

EXAMPLE 8

Using a catalyst mixture comprising 6–25 mmoles of ethyl iodide per 21.9 mmoles of triethylaluminum and one mmole vanadium oxytrichloride, methyl bromide was reacted with triethylaluminum at 75° C. for about 20 hours to produce effective yields of ethyl bromide and trimethylaluminum. Substituting trimethylaluminum for triethylaluminum in the catalyst mixture resulted in improved reaction rates with exchange substantially completed in five hours at 75° C.

The successful exchange reactions employed EtI:-VOCl$_3$:R$_3$Al ratio of 12.4:1.0:1.0 for R=Et and a 1.0:1.0:2.0 ratio for R=Me. The catalyst mix was prepared by adding 1.0 mmole of VOCl$_3$ to 12.5 mmoles EtI, followed by the addition of 1.0 mmole of Et$_3$Al. If the excess EtI was evaporated at this point from the black slurry, the black residue that remained was not an effective catalyst for the Et$_3$Al-MeBr exchange. The same procedure was followed when using Me$_3$Al as a catalyst component. Evaporation of excess EtI also left a black residue. In this case, however, the residue was an effective catalyst after 6.25 mmoles of EtI had been added to the Et$_3$Al solution.

The foregoing disclosure and description of the invention is illustrative and explanatory thereof and various changes may be made within the scope of the appended claims without departing from the spirit of the invention.

What is claimed is:

1. A method of making trimethylaluminum, comprising reacting trialkylaluminum having at least two carbon atoms in the alkyl group with a methyl halide in the presence of a vanadium-based catalyst to form trimethylaluminum and an alkyl halide, said vanadium-based catalyst comprising a vanadium compound, an aluminum alkyl compound and an alkyl iodide.

2. The method of claim 1, wherein the trialkylaluminum reactant is triethylaluminum.

3. The method of claim 1, wherein the methyl halide is methyl bromide.

4. The method of claim 1, wherein the methyl halide is methyl chloride.

5. The method of claim 1, wherein the vanadium-based catalyst was prepared using vanadium oxytrichloride.

6. The method of claim 1, wherein the vanadium-based catalyst is prepared by the addition of an aluminum alkyl compound to a solution of alkyl iodide and a vanadium compound.

7. The method of claim 6, wherein the aluminum alkyl compound of the catalyst is selected from the group consisting of trimethylaluminum, triethylaluminum, tri-isobutylaluminum, tri-n-butylaluminum, tri-n-hexylaluminum, tri-n-octylaluminum, diethylaluminum iodide and diethylaluminum chloride.

8. The method of claim 6, wherein the aluminum alkyl compound of the catalyst is triethylaluminum or trimethylaluminum.

9. The method of claim 6, wherein the alkyl iodide may have from one to 18 carbon atoms in the alkyl group.

10. The method of claim 6, wherein the alkyl iodide of the catalyst is ethyl iodide or methyl iodide.

11. The method of claim 6, wherein the vanadium compound of the catalyst is selected from the group consisting of vanadium oxytrichloride, vanadium oxytribromide, vanadium trichloride and vanadium tribromide.

12. The method of claim 6, wherein the vanadium compound of the catalyst is selected from the group consisting of vanadium alkylates and vanadium oxyalkylates.

13. The method of claim 6, wherein the vanadium compound in the catalyst is vanadium oxytrichloride.

14. The method of claim 1, wherein the reaction is carried out at a temperature of from about $-20°$ C. to about 200° C.

15. The method of claim 1, wherein the reaction is carried out at a temperature of from about 0° C. to about 150° C.

16. The method of claim 1, wherein the reaction is carried out at a temperature of about 65°–75° C.

17. The method of claim 1, wherein the reaction is carried out for up to about 24 hours until the exchange has been completed.

18. A method of making trimethylaluminum, comprising the following catalyzed reaction:

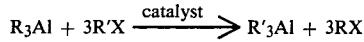

wherein
R = $C_2$–$C_4$ alkyl group
R' = $CH_3$
X = Br or Cl
Catalyst = alkyl iodide-vanadium compound-trialkylaluminum mixture.

19. The method of claim 18, wherein R is a $C_2H_5$ group.

20. The method of claim 18, wherein R'X is methyl bromide.

21. The method of claim 18, wherein R'X is methyl chloride.

22. The method of claim 18, wherein the catalyst functions to convert R'X to methyl iodide.

23. The method of claim 1, wherein the reaction is carried out in the presence of an excess of methyl halide.

24. The method of claim 23, wherein the methyl halide is methyl chloride or methyl bromide.

25. The method of claim 1, wherein the reaction is carried out in the presence of an aliphatic hydrocarbon solvent.

26. The method of claim 25, wherein the hydrocarbon solvent is selected from the group consisting of hexane, cyclohexane and decane.

27. A method of making trimethylaluminum, comprising reacting triethylaluminum and methyl chloride or methyl bromide in the presence of a vanadium-based catalyst comprising a mixture of ethyl iodide, vanadium oxytrichloride and triethylaluminum.

* * * * *